United States Patent
Murooka et al.

(10) Patent No.: US 10,962,400 B2
(45) Date of Patent: Mar. 30, 2021

(54) MEASUREMENT SYSTEM, AND MEASUREMENT METHOD

(71) Applicant: FUJIFILM Corporation, Tokyo (JP)

(72) Inventors: Takashi Murooka, Ashigarakami-gun (JP); Yi Hu, Ashigarakami-gun (JP); Yasutomo Goto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 701 days.

(21) Appl. No.: 15/697,910

(22) Filed: Sep. 7, 2017

(65) Prior Publication Data

US 2018/0058904 A1  Mar. 1, 2018

Related U.S. Application Data

(63) Continuation of application No. PCT/JP2016/055381, filed on Feb. 24, 2016.

(30) Foreign Application Priority Data

Mar. 10, 2015 (JP) ............................. JP2015-047621

(51) Int. Cl.
*G01F 23/292* (2006.01)
*A61M 37/00* (2006.01)
(Continued)

(52) U.S. Cl.
CPC ............ *G01F 23/292* (2013.01); *A61M 37/00* (2013.01); *G01B 11/00* (2013.01); *G01B 11/24* (2013.01);
(Continued)

(58) Field of Classification Search
CPC ....... G01F 23/292; G01F 22/00; G01B 11/22; G01B 11/24; A61M 37/0015
(Continued)

(56) References Cited

U.S. PATENT DOCUMENTS 7,323,705 B2   1/2008  Haga et al.
2004/0031335 A1  2/2004  Fromme et al.
(Continued)

FOREIGN PATENT DOCUMENTS

JP   62-237323 A   10/1987
JP   2001-133309 A   5/2001
(Continued)

OTHER PUBLICATIONS

Communication dated Oct. 2, 2018 from the Japanese Patent Office in counterpart Japanese application No. 2015-047621.
(Continued)

*Primary Examiner* — Kevin K Pyo
(74) *Attorney, Agent, or Firm* — Sughrue Mion, PLLC

(57) ABSTRACT

There is provided a measurement system that measures the volume of a drug solution that fills a needle-shaped recess of a mold. A measurement unit of the measurement system measures respective heights of a plurality of measurement points which are stored in a storage unit and are preset on a plane parallel to the mold, in a direction orthogonal to the plane. A surface shape calculation unit calculates a three-dimensional shape of the surface of the drug solution on the basis of the heights of the plurality of measurement points measured by the measurement unit. A volume calculation unit calculates the volume of the drug solution that fills the needle-shaped recess on the basis of the three-dimensional shape of the surface of the drug solution calculated by the surface shape calculation unit and the shape of the needle-shaped recess of the mold.

25 Claims, 13 Drawing Sheets

(51) Int. Cl.
*G01B 11/00* (2006.01)
*G01F 23/00* (2006.01)
*G01F 22/00* (2006.01)
*G01B 11/24* (2006.01)

(52) U.S. Cl.
CPC .......... *G01F 22/00* (2013.01); *G01F 23/0061* (2013.01); *G01F 23/2928* (2013.01); *A61M 37/0015* (2013.01); *A61M 2037/0023* (2013.01); *A61M 2037/0053* (2013.01); *A61M 2205/3306* (2013.01); *A61M 2205/3382* (2013.01); *A61M 2205/50* (2013.01); *A61M 2207/10* (2013.01)

(58) Field of Classification Search
USPC .......................................... 250/574, 576, 577
See application file for complete search history.

(56) References Cited

U.S. PATENT DOCUMENTS

| | | | |
|---|---|---|---|
| 2008/0304082 A1 | 12/2008 | Gotz et al. | |
| 2012/0051660 A1 | 3/2012 | Lee et al. | |
| 2014/0313524 A1 | 10/2014 | Banyay et al. | |
| 2018/0058903 A1* | 3/2018 | Hu | G01F 22/00 |

FOREIGN PATENT DOCUMENTS

| | | |
|---|---|---|
| JP | 2004-12302 A | 1/2004 |
| JP | 2008-224673 A | 9/2008 |
| JP | 2011-224332 A | 11/2011 |
| JP | 2012-254952 A | 12/2012 |
| JP | 2013-162982 A | 8/2013 |
| JP | 2013-234229 A | 11/2013 |
| JP | 2014-531578 A | 11/2014 |

OTHER PUBLICATIONS

Communication dated Mar. 8, 2018 from the European Patent Office in counterpart application No. 16761485.8.
"Geometric data analysis", Wikipedia, May 27, 2014, Retrieved from the internet on Feb. 19, 2018, URL: https://en.wikipedia.org/w/index.php?title=Geometric_data_analysis&oldid=610307299. (1 page total).
"Bioassay", Wikipedia, Jan. 27, 2015, Retrieved from the internet on Feb. 9, 2018, URL: https://en.wikipedia.org/w/index.php?title=Bioassay&oldid=644423738. (4 page total).
Communication dated Jan. 31, 2018 from the Japanese Patent Office in counterpart Japanese application No. 2015-047621.
Communication dated Mar. 10, 2020 from the European Patent Office in application No. 16761485.8.
International Preliminary Report on Patentability issued from the International Bureau in counterpart International Application No. PCT/JP2016/055381, dated Sep. 12, 2017.
Translation of Written Opinion dated May 24, 2016, issued by the International Bureau in counterpart Application No. PCT/JP2016/055381.
International Search Report dated May 24, 2016, issued by the International Bureau in counterpart Application No. PCT/JP2016/055381.

* cited by examiner

FIG. 8A
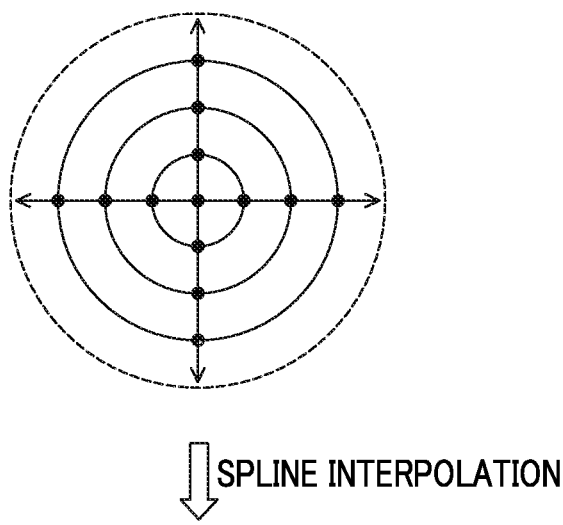
⇩ SPLINE INTERPOLATION
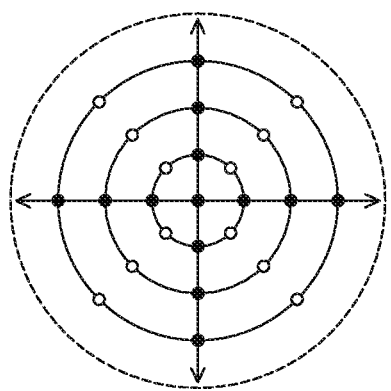
FIG. 8 B

FIG. 10A
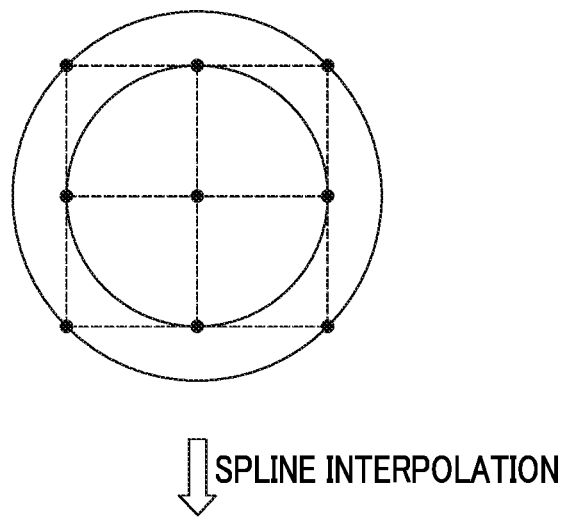
⇩ SPLINE INTERPOLATION
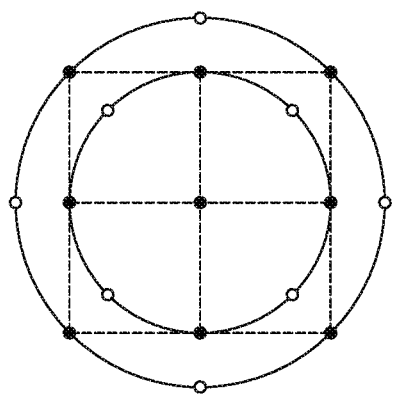
FIG. 10B

MEASUREMENT SYSTEM, AND MEASUREMENT METHOD

CROSS-REFERENCE TO RELATED APPLICATIONS

This application is a Continuation of PCT International Application No. PCT/JP2016/055381 filed on Feb. 24, 2016, which claims priority under 35 U.S.C. § 119(a) to Japanese Patent Application No. 2015-047621 filed on Mar. 10, 2015. Each of the above applications is hereby expressly incorporated by reference, in their entirety, into the present application.

BACKGROUND OF THE INVENTION

1. Field of the Invention

The present invention relates to a measurement system, a measurement method, and a measurement program, and particularly, to a technique that measures the amount of a drug solution that fills each needle-shaped recess of a sheet-shaped mold in which a plurality of the needle-shaped recesses, the needle-shaped recesses being an inverted type of a micro-needle, are formed or the amount of a drug after the filled drug solution is dried.

2. Description of the Related Art

In recent years, as a new agent mold capable of dosing a drug such as insulin, vaccines, or human growth hormone (hGH) into the skin without causing pains, a micro-needle array (hereinafter, simply referred to as an "MNA") is known. The MNA is a device that contains a drug, in which biodegradable micro-needles (also referred to as fine needles) are arranged in an array shape. By attaching the MNA to the skin, each micro-needle pierces the skin, and thus, the micro-needles are absorbed into the skin. Thus, it is possible to dose the drug contained in each micro-needle into the skin.

As a method for manufacturing such an MNA, a method for filling a solution drug (a drug solution obtained by dissolving a drug or the like into water) in each needle-shaped recess of a mold having multiple needle-shaped recesses, the needle-shaped recesses being an inverted type of a micro-needle, drying the solution drug to form an MNA, and then, separating the MNA from the mold (JP2013-162982A). In manufacturing the MNA, it is necessary to strictly manage the amount of a drug dosed in the skin by the MNA.

As a method for measuring the amount of a drug contained in the MNA, for example, the method for measuring the weight of a mold before filling of the drug and the amount of the mold after filling of the drug using a highly accurate electronic balance, and then calculating a weight difference before filling and after filling to measure the weight of the drug is known.

On the other hand, JP2011-224332A discloses a method for forming a needle portion as a conical column, measuring the height and the diameter of the needle portion, setting a specific weight of a polymer material and a specific weight of a drug to 1, respectively, and calculating the amount of a drug in the needle portion.

Further, JP2012-254952A discloses a method for observing a two-layer micro-needle including a first portion that contains a drug and a second portion that does not contain a drug using a video microscope, and measuring the length of the first portion colored with blue from a tip thereof.

SUMMARY OF THE INVENTION

However, in a case where measurement of the weight of a drug is performed using the above-described electronic balance with high accuracy, since the weight of the drug is small compared with the weight of the mold, for example, since the weight of the drug is one several hundredth of the weight of the mold, it is not possible to measure the weight of the drug with high accuracy on the basis of a weight difference between the mold before filling of the drug and the mold after filling of the drug.

Further, in the method disclosed in JP2011-224332A, the needle portion is formed as the conical column, the height and the diameter of the needle portion are measured, and the volume of the needle portion is calculated, but there are many cases where a base end surface of the conical column-shaped needle portion that contains a drug does not form a horizontal circular surface. Further, there is also a case where the needle portion of the MNA after being separated from the mold has a curved tip. Thus, it is difficult to calculate the volume of the needle portion with high accuracy on the basis of the height and the diameter of the measured needle portion.

In addition, as disclosed in JP2012-254952A, if the shape of the two-layer micro-needle including the first portion that contains a drug and the second portion that does not contain a drug is already known, it is possible to calculate the volume of the first portion by measuring the length of the first portion colored with blue from the tip thereof, but, as disclosed in JP2011-224332A, it is not guaranteed that a boundary between the first portion and the second portion is formed as a horizontal surface. Further, there is also a case where the first portion of the micro-needle of the MNA after being separated from the mold has a curved tip. Thus, it is difficult to calculate the volume of the first portion with high accuracy although the length of the first portion from the tip thereof is measured with high accuracy.

The invention has been made in consideration of such a problem, an object of the invention is to provide a measurement system, a measurement method, and a measurement program capable of measuring the amount of a drug solution that fills a needle-shaped recess of a mold or the amount of a drug after the filled drug solution is dried in a non-destructive manner with high accuracy before a micro-needle array is separated from the mold.

According to an aspect of the invention to achieve the object described above, there is provided a measurement system that measures an amount of a drug solution that fills each needle-shaped recess of a sheet-shaped mold in which a plurality of the needle-shaped recesses are formed, the needle-shaped recesses being an inverted type of a micro-needle, or an amount of a drug after the filled drug solution is dried, the system comprising: a measurement unit that measures respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried; a surface shape calculation unit that calculates a three-dimensional shape of the surface of the drug solution or the surface of the drug on the basis of the heights of the plurality of measurement points measured by the measurement unit; and a volume calculation unit that calculates the volume of the drug solution that fills the needle-shaped recess or the drug after the filled drug solution is dried on the basis of the three-dimensional shape of the surface of the drug solution or the surface of the drug, calculated by the surface shape calculation unit, and the shape of the needle-shaped recess of the mold.

In many cases, the surface of the drug solution that fills the needle-shaped recess or the surface of the drug after the filled drug solution is dried is not a horizontal surface. According to this aspect of the invention, the heights of the plurality of measurement points on the surface of the drug solution that fills the needle-shaped recess or the surface of the drug are respectively measured, and the three-dimensional shape of the surface of the drug solution or the surface of the drug is calculated on the basis of the measured heights of the plurality of measurement points. Here, the number of the plurality of preset measurement points is equal to or greater than a number necessary for calculating the three-dimensional shape of the surface. However, if the number is excessively large, the measurement time becomes long. Thus, it is preferable that the number is set as an appropriate number in consideration of the measurement time. Further, the volume of the drug solution that fills the needle-shaped recess or the drug after the filled drug solution is dried is calculated on the basis of the calculated three-dimensional shape of the surface and the shape (known shape) of the needle-shaped recess of the mold. Thus, it is possible to measure the volume of the drug solution that fills the needle-shaped recess of the mold or the drug after the filled drug solution is dried in a non-destructive manner with high accuracy, and to calculate the amount of the drug solution or the amount of the drug with high accuracy from the measured volume.

In a measurement system according to another aspect of the invention, it is preferable that the plurality of preset measurement points include a plurality of measurement points disposed at equal intervals on a scanning line.

In a measurement system according to still another aspect of the invention, it is preferable that the plurality of preset measurement points are symmetrical with respect to a central position of the needle-shaped recess and correspond to a plurality of positions disposed at equal intervals on concentric circles in which the central position is the center. As a feature of the shape of the surface of the drug solution that fills the needle-shaped recess or the drug after the filled drug solution is dried, there is a feature that the shape is biased in an arbitrary direction, and the biasing feature has continuity in a radial direction and a concentric circle direction of the center of opening of the needle-shaped recess. Thus, by narrowing down a plurality of preset measurement points into important measurement points in accordance with the feature of the shape of the surface in this way, it is possible to reduce the number of measurement points, and to prevent the accuracy of the calculated shape of the surface from being lowered.

In a measurement system according to still another aspect of the invention, it is preferable that the plurality of preset measurement points correspond to a plurality of positions disposed on two lines that are orthogonal to each other at the central position of the needle-shaped recess. With this configuration, it is possible to set the number of the plurality of preset measurement points to a minimum, and to prevent the accuracy of the calculated shape of the surface from being lowered.

In a measurement system according to still another aspect of the invention, it is preferable that the measurement system further includes an evaluation point calculation unit that interpolates measurement results of the plurality of measurement points in at least one direction among a deflection angle direction and a radial direction in a polar coordinate space in which the central position of the needle-shaped recess is the origin of polar coordinates to calculate new evaluation points, and that the calculated new evaluation points are added to the plurality of measurement points. With this configuration, it is possible to reduce the number of measurement points to be measured, and to increase the number of measurement points to be used for calculation of the shape of the surface.

In a measurement system according to still another aspect of the invention, it is preferable that the surface shape calculation unit performs non-linear interpolation with respect to three-dimensional positions of the plurality of measurement points specified by positions of the plurality of measurement points on the plane and the heights of the plurality of measurement points measured by the measurement unit to calculate the three-dimensional shape of the surface of the drug solution or the surface of the drug. That is, since the shape of the surface of the drug solution that fills the needle-shaped recess or the drug after the filled drug solution is dried is a curve, in a case where the shape of the surface is calculated from the three-dimensional positions of the plurality of specified measurement points, it is preferable to non-linearly interpolate the three-dimensional positions of the plurality of measurement points.

In a measurement system according to still another aspect of the invention, it is preferable that the non-linear interpolation is any one of polynomial interpolation of a second or higher order, spline interpolation, and Lagrange interpolation.

In a measurement system according to still another aspect of the invention, it is preferable that the surface shape calculation unit performs, in performing the non-linear interpolation with respect to the three-dimensional positions of the plurality of measurement points, non-linear interpolation that satisfies feature information indicating a feature of the three-dimensional shape of the surface of the drug solution or the surface of the drug to calculate the three-dimensional shape of the surface of the drug solution or the surface of the drug. The feature information indicating the feature of the three-dimensional shape of the surface of the drug solution or the surface of the drug may include, for example, unevenness conditions of the surface of the drug solution or the surface of the drug. In a case where the three-dimensional positions of the plurality of measurement points are non-linearly interpolated, by performing the non-linear interpolation that satisfies the feature information indicating the feature of the three-dimensional shape of the surface of the drug solution or the surface of the drug, it is possible to calculate the shape of the surface of the drug solution or the surface of the drug with high accuracy.

In a measurement system according to still another aspect of the invention, it is preferable that the surface shape calculation unit calculates the three-dimensional shape of the surface of the drug solution or the surface of the drug, using three-dimensional positions of the plurality of measurement points specified by positions of the plurality of measurement points on the plane and the heights of the plurality of measurement points measured by the measurement unit, and using predict information relating to the three-dimensional shape of the surface of the drug solution or the surface of the drug. The predict information relating to the three-dimensional shape of the surface of the drug solution or the surface of the drug may include main component analysis (singular value decomposition), recursive filtering, independent component analysis, fractal analysis, or the like, with respect to main components generated on the basis of surface shapes of a plurality of models which are measured in advance with high accuracy.

In a measurement system according to still another aspect of the invention, it is preferable that the surface shape calculation unit calculates the three-dimensional shape of the surface of the drug solution or the surface of the drug by causing three-dimensional positions of the plurality of measurement points specified by positions of the plurality of measurement points on the plane and the heights of the plurality of measurement points measured by the measurement unit to be fitted to a model including a feature amount of the three-dimensional shape of the surface of the drug solution or the surface of the drug, which is measured in advance, to calculate the three-dimensional shape of the surface of the drug solution or the surface of the drug. With this configuration, it is possible to reduce the number of the plurality of measurement points, and to calculate the three-dimensional shape of the surface of the drug solution or the surface of the drug with high accuracy.

In a measurement system according to still another aspect of the invention, it is preferable that the model including the feature amount of the three-dimensional shape is formed by main component coefficient vectors extracted from a plurality of three-dimensional shapes obtained in advance by measurement of a plurality of samples on the surface of the drug solution or the surface of the drug.

In a measurement system according to still another aspect of the invention, it is preferable that the measurement unit is a confocal microscope that measures the heights on the surface of the drug solution that fills the needle-shaped recess or on the surface of the dried drug after filling using a confocal optical system, or a triangulation type displacement meter that measures the heights on the surface of the drug solution that fills the needle-shaped recess or on the surface of the dried drug after filling using a triangulation method.

According to still another aspect of the invention, there is provided a measurement method for measuring the amount of a drug solution that fills each needle-shaped recess of a sheet-shaped mold in which a plurality of the needle-shaped recesses are formed, the needle-shaped recesses being an inverted type of a micro-needle, or the amount of a drug after the filled drug solution is dried, the method comprising: a step of measuring respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried; a step of calculating a three-dimensional shape of the surface of the drug solution or the surface of the drug on the basis of the measured heights of the plurality of measurement points; and a step of calculating the volume of the drug solution that fills the needle-shaped recess or the drug after the filled drug solution is dried on the basis of the calculated three-dimensional shape of the surface of the drug solution or the surface of the drug and the shape of the needle-shaped recess of the mold.

In a measurement method according to still another aspect of the invention, it is preferable that the plurality of preset measurement points include a plurality of measurement points disposed at equal intervals on a scanning line.

In a measurement method according to still another aspect of the invention, it is preferable that the plurality of preset measurement points are symmetrical with respect to a central position of the needle-shaped recess and correspond to a plurality of positions disposed at equal intervals on concentric circles in which the central position is the center.

According to still another aspect of the invention, there is provided a measurement program for measuring an amount of a drug solution that fills each needle-shaped recess of a sheet-shaped mold in which a plurality of the needle-shaped recesses are formed, the needle-shaped recesses being an inverted type of a micro-needle, or an amount of a drug after the filled drug solution is dried, the program causing a computer to execute: a step of measuring respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried; a step of calculating a three-dimensional shape of the surface of the drug solution or the surface of the drug on the basis of the measured heights of the plurality of measurement points; and a step of calculating the volume of the drug solution that fills the needle-shaped recess or the drug after the filled drug solution is dried on the basis of the calculated three-dimensional shape of the surface of the drug solution or the surface of the drug and the shape of the needle-shaped recess of the mold.

In a measurement program according to still another aspect of the invention, it is preferable that the plurality of preset measurement points include a plurality of measurement points disposed at equal intervals on a scanning line.

In a measurement program according to still another aspect of the invention, it is preferable that the plurality of preset measurement points are symmetrical with respect to a central position of the needle-shaped recess and correspond to a plurality of positions disposed at equal intervals on concentric circles in which the central position is the center. A computer-readable non-transitory tangible recording medium on which the measurement programs are recorded is also included in an aspect of the invention.

According to the invention, it is possible to measure the amount of a drug solution that fills a needle-shaped recess of a mold or the amount of a drug after the filled drug solution is dried in a non-destructive manner with high accuracy before a micro-needle array is separated from the mold.

BRIEF DESCRIPTION OF THE DRAWINGS

FIGS. 8A and 8B are diagrams showing an embodiment in a case where a new point (evaluation point) is calculated by interpolation of a plurality of measurement points.

FIGS. 10A and 10B are diagrams showing a second embodiment of a plurality of measurement points.

DESCRIPTION OF THE PREFERRED EMBODIMENTS

Hereinafter, preferred embodiments of a measurement system, a measurement method, and a measurement program according to the present invention will be described with reference to the accompanying drawings.

First, a method for manufacturing a percutaneous absorption sheet (an MNA sheet) including a polymer layer (a first polymer layer) that contains a drug in a micro-needle array (MNA) will be described.

FIGS. 1A-1D are diagrams showing a method for manufacturing an MNA sheet, and particularly, is a diagram showing a formation process of the first polymer layer.

Figure 1A:
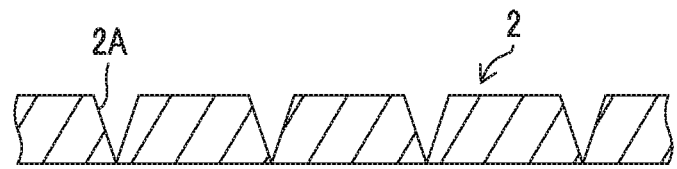
FIGS. 1A to 1D are diagrams showing a method for manufacturing an MNA sheet.

As shown in FIG. 1A, a sheet-shaped mold 2 in which a plurality of needle-shaped recesses 2A having an inverted shape of an MNA is prepared. The needle-shaped recess 2A is formed in a downward conical shape, for example, and a fine air vent port (see FIG. 2A) is formed at a top portion thereof.

Figure 1B:
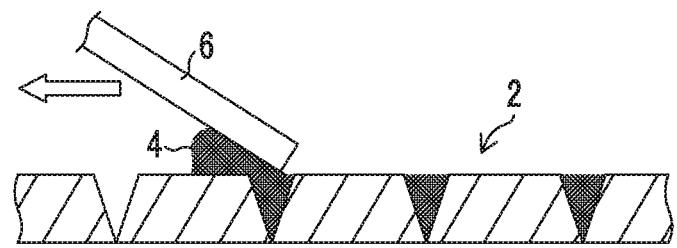
Figure 1C:
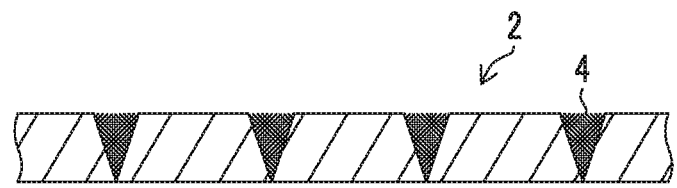

Subsequently, as shown in FIG. 1B, a first polymer solution (hereinafter, simply referred to as a "drug solution") 4 including a drug is provided onto a mold 2, and the needle-shaped recess 2A is filled with the drug solution 4 by providing a suction force through the air vent port and moving a squeegee 6 along a front surface of the mold 2. FIG. 1C shows a state immediately after the drug solution 4 fills the needle-shaped recesses 2A of the mold 2.

Figure 1D:
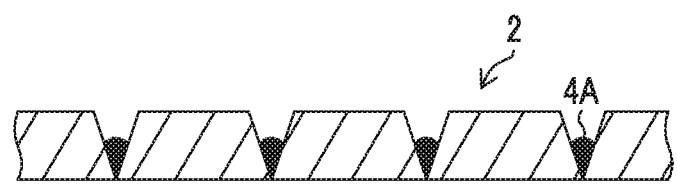

Then, a dried drug (a first polymer layer) 4A is formed through a drying process of drying the filled drug solution 4 (FIG. 1D).

Thereafter, a polymer layer (a second polymer layer) that does not include a drug, a support, or the like are formed, and then, an MNA sheet formed by the first polymer layer, the second polymer layer, and the support is separated from the mold 2. In this way, the MNA sheet is formed.

Figure 2A:
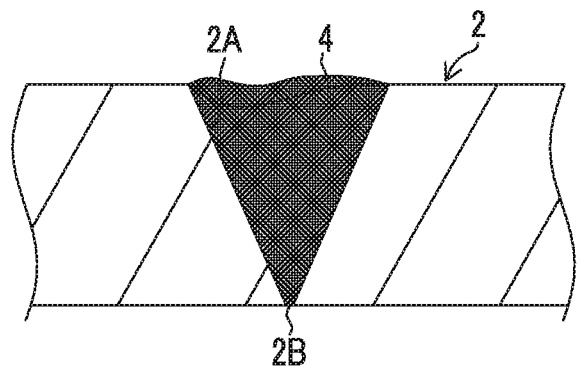
FIGS. 2A to 2C are diagrams showing a surface shape or the like of a drug solution immediately after the drug solution fills a needle-shaped recess of a mold.
Figure 2B:
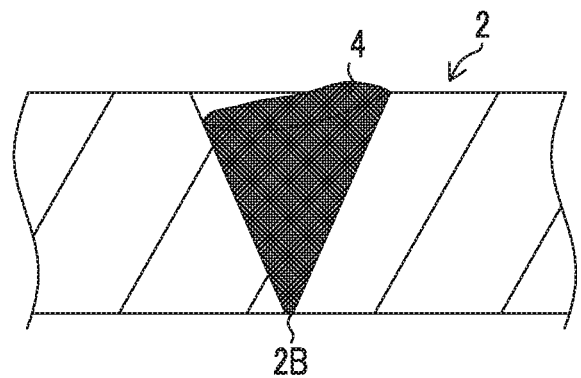
Figure 2C:
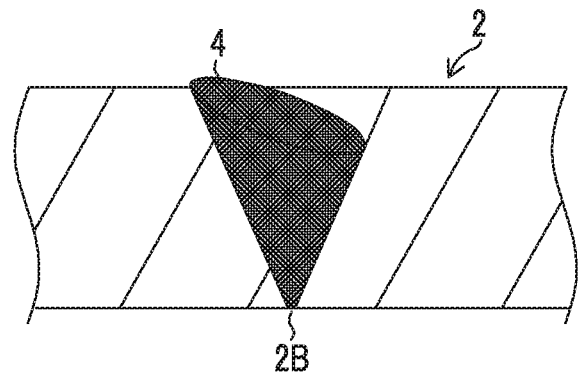

FIGS. 2A to 2C show a surface shape or the like of the drug solution 4 immediately after the drug solution 4 fills each needle-shaped recess 2A of the mold 2. Here, a reference numeral 2B represents an air vent port in FIGS. 2A to 2C. The diameter of the air vent portion 2B is about 30 μm, and the drug solution 4 does not flow out of the air vent port 2B.

As shown in FIGS. 2A to 2C, the surface shape of the drug solution 4 that fills the needle-shaped recess 2A does not have a horizontal surface that is aligned with the front surface of the mold 2 as shown in FIG. 1C, and has a concave shape, a convex shape, an inclined shape, and various combinations thereof.

The invention is provided to calculate the volume of the drug solution 4 (or the drug 4A) that fills the needle-shaped recess 2A of the mold 2 and to measure the amount of the drug solution 4 that fills the needle-shaped recess 2A of the mold 2 or the amount of the drug 4A after the filled drug solution 4 is dried.

[Measurement System]

Next, an embodiment of the measurement system according to the invention will be described. Hereinafter, a case where the volume of the drug solution 4 (the drug solution 4 immediately after filling) that fills the needle-shaped recess 2A of the mold 2 is measured will be described, but the volume of the drug solution 4 during drying or the volume of the drug 4A after drying may be measured in a similar manner.

Figure 3:
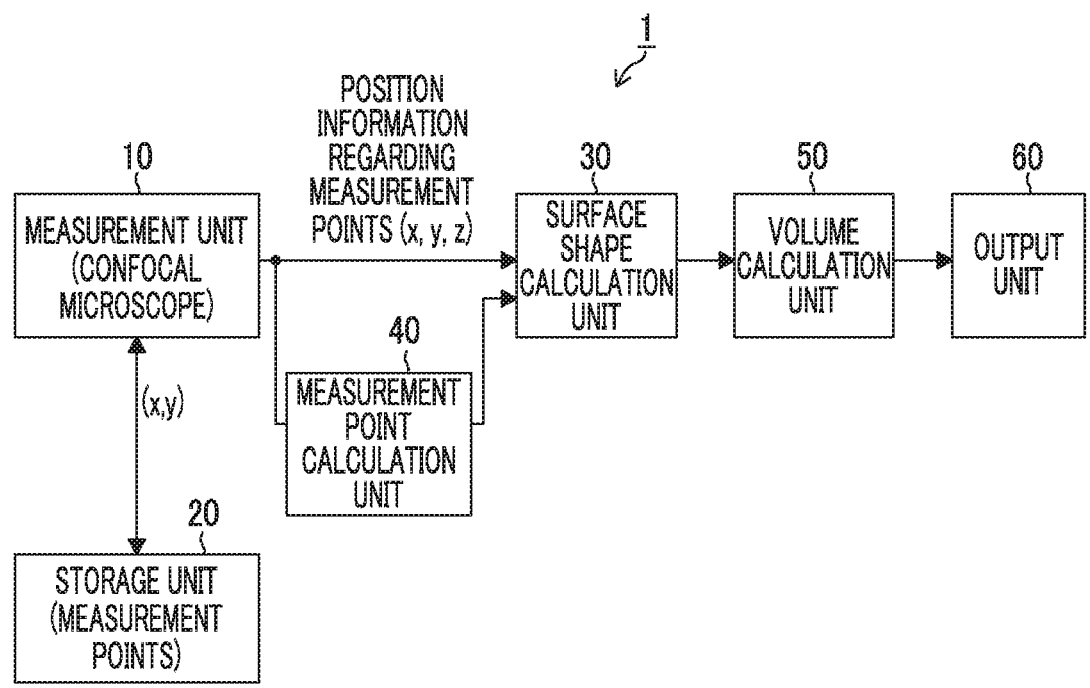
FIG. 3 is a block diagram showing an embodiment of a measurement system according to the invention.

FIG. 3 is a block diagram showing an embodiment of the measurement system according to the invention.

As shown in FIG. 3, the measurement system 1 includes a measurement unit 10, a storage unit 20, a surface shape calculation unit 30, an evaluation point calculation unit 40, a volume calculation unit 50, and an output unit 60, as main components.

The measurement unit 10 calculates the heights of a plurality of points of the drug solution 4, and for example, may employ a confocal microscope.

Figure 4:
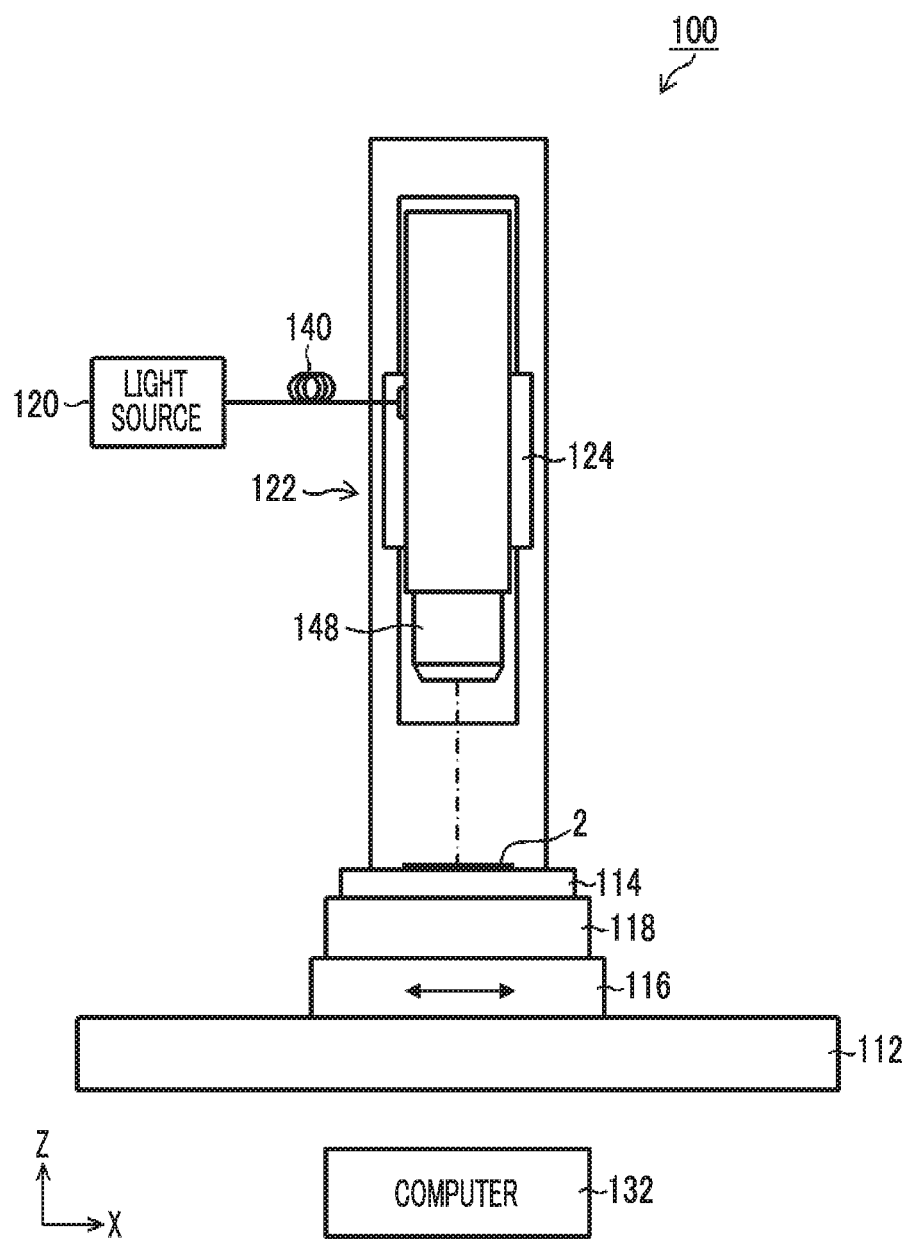
FIG. 4 is a front view showing an embodiment of a confocal microscope that is applicable as a measurement unit.

FIG. 4 is a front view showing an embodiment of a confocal microscope 100 that is applicable as the measurement unit 10.

The confocal microscope 100 shown in FIG. 4 is an apparatus that measures a surface shape of a measurement target (drug solution 4) using a confocal optical system in a non-contact manner, and includes, as main components, a base 112, a table 114 that supports the mold 2 filled with the drug solution 4, a table movement unit 116 that moves the table 114 along an X-axial direction and a Y-axial direction on an XY plane (horizontal surface), a position detection unit (not shown) that detects positions of the table 114 in the X-axial direction and the Y-axial direction, a table tilt unit 118 that tilts the table 114 around an X-axis and a Y-axis, a tilt angle detection unit (not shown)) that detects tilt angles of the table 114 around the X-axis and the Y-axis, a light source 120 that emits laser light, a measurement unit main body 122, a Z-axis movement unit 124 that moves the measurement unit main body 122 along a Z-axial direction (vertical direction), a Z-axial direction position detection unit 134Z (FIG. 5) that detects the position of the measurement unit main body 122 in the Z-axial direction, and a computer 132 that controls entire operations and performs various calculation processes. A display which serves as a display unit, a keyboard and a mouse which serve as an operation unit, and a hard disk drive device which serves as a storage unit are connected to the computer 132.

Figure 5:
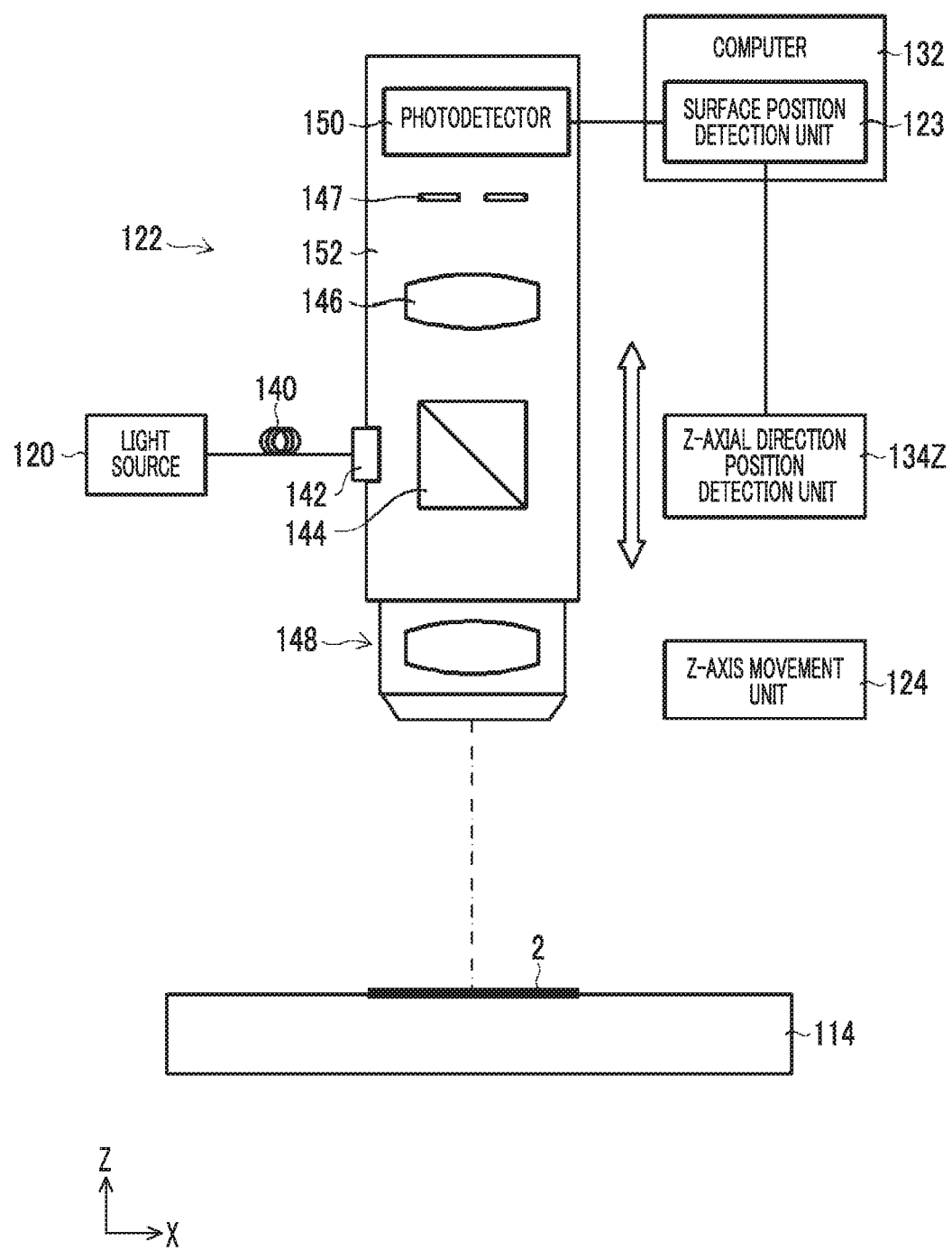
FIG. 5 is a diagram showing a schematic configuration of a measurement unit main body including a light source of the confocal microscope.

FIG. 5 is a diagram showing a schematic configuration of the measurement unit main body 122 including the light source 120 of the confocal microscope 100.

The measurement unit main body 122 includes a collimator 142, a beam splitter 144, an imaging lens 146, a pinhole plate 147, an objective lens 148, and a photodetector

150. The respective components of the measurement unit main body 122 are integrally provided in the measurement unit main body 152.

The light source 120 is configured by a light source that emits monochromatic light, and for example, includes a monochromatic laser light source. Light emitted from the light source 120 propagates to the measurement unit main body 122 through a light guide 140.

The collimator 142 converts the light propagated from the light source 120 through the light guide 140 into parallel light to be then incident to the beam splitter 144. The beam splitter 144 reflects the light output from the collimator 142 to be incident to the objective lens 148.

The objective lens 148 concentrates the light output from the beam splitter 144 to be then irradiated onto a surface of the drug solution 4 (see FIGS. 2A-2C) that fills the mold 2, which is a measurement target surface.

The light reflected from the surface of the drug solution 4 is incident to the beam splitter 144 through the objective lens 148 again, and passes through the beam splitter 144 to be incident to the imaging lens 146.

The imaging lens 146 concentrates the light passed through the beam splitter 144 to be then incident to the photodetector 150.

The pinhole plate 147 includes a pinhole and is disposed at a focal position of the imaging lens 146. The light concentrated by the imaging lens 146 passes through the pinhole of the pinhole plate 147 to be then incident to the photodetector 150.

The photodetector 150 converts the intensity of the received light into an electric signal and outputs the result to the computer 132.

Using the confocal optical system having the above-described configuration, it is possible to obtain information about the height (position in the Z-axial direction) of the surface of the drug solution 4. Hereinafter, its principle will be briefly described.

If the measurement unit main body 122 is moved in the Z-axial direction by the Z-axis movement unit 124, the focal position of the objective lens 148 is changed.

If the focus of the objective lens 148 is formed on the surface of the drug solution 4, the light concentrated by the imaging lens 146 forms a focus at the position of the pinhole of the pinhole plate 147. Thus, almost the entirety of light reflected from the surface of the drug solution 4 passes through the pinhole of the pinhole plate 147. Accordingly, if the focus of the objective lens 148 is formed on the surface of the drug solution 4, the intensity of light received by the photodetector 150 becomes a maximum.

On the other hand, in a state where the focus of the objective lens 148 deviates from the surface of the drug solution 4, the light concentrated by the imaging lens 146 is focused at a position deviated from the pinhole plate 147. Thus, part of the light reflected from the surface of the drug solution 4 cannot pass the pinhole. Accordingly, if the focus of the objective lens 148 deviates from the surface of the drug solution 4, the intensity of the light received by the photodetector 150 is noticeably lowered.

In this way, the intensity of the light detected by the photodetector 150 becomes a maximum when the focus of the objective lens 148 is formed on the surface of the drug solution 4. Accordingly, if the Z-axial direction position of the measurement unit main body 122 is detected when the intensity of the light detected by the photodetector 150 becomes maximum, it is possible to unmistakably calculate the Z-axial direction position of the measurement point of the surface of the drug solution 4.

The computer 132 executes a predetermined program to function as the surface position detection unit 123, and detect a position z of the measurement point in the Z-axial direction on the basis of the intensity of the light detected by the photodetector 150 and the position of the measurement unit main body 122 in the Z-axial direction detected by the Z-axial direction position detection unit 134Z.

Further, the computer 132 executes a predetermined program to function as a scanning control unit that moves the table movement unit 116 and irradiates measurement light to a desired measurement point (a measurement point (x, y) on the XY plane) on the surface of the drug solution 4. Thus, it is possible to detect a three-dimensional position (x, y, z) on the surface of the drug solution 4 from the position (x, y) of the measurement point on the XY plane where the measurement light is irradiated and the position z of the measured measurement point in the Z-axial direction.

Here, it is possible to calculate a surface shape (three-dimensional shape) of the drug solution 4 by scanning the surface of the drug solution 4 and measuring three-dimensional positions (x, y, z) of multiple measurement points, but in a case where the multiple measurement points are measured, there is a problem in that a measurement time becomes long. The invention is provided to reduce the number of measurement points as much as possible, and to calculate the surface shape of the drug solution 4 with high accuracy.

Position information (x, y) of a plurality of measurement points to be measured on the surface of the drug solution 4 is stored in advance in the storage unit 20 shown in FIG. 3.

Embodiment of a Plurality of Measurement Points

Then, an embodiment of a plurality of measurement points to be stored (set) in advance in the storage unit 20 will be described.

First Embodiment of a Plurality of Measurement Points

Figure 6A:
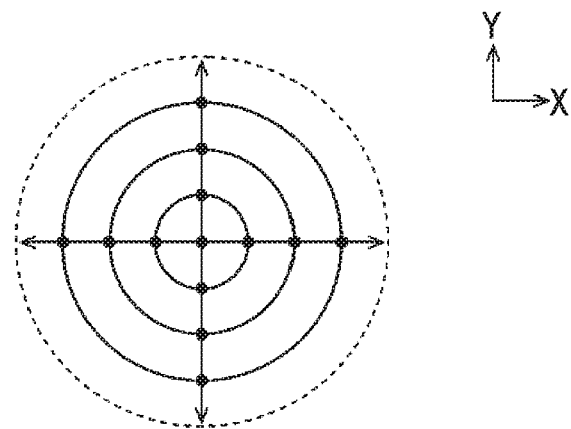
FIGS. 6A and 6B are diagrams showing a first embodiment of a plurality of measurement points.
Figure 6B:
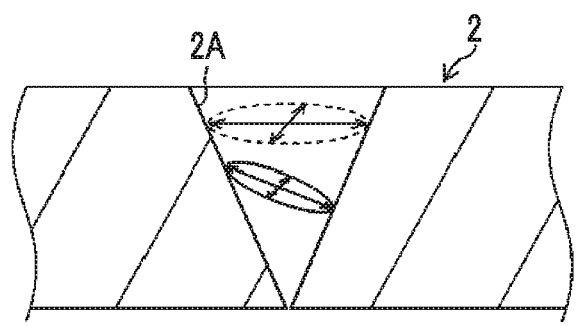

FIGS. 6A and 6B are diagrams showing a first embodiment of a plurality of measurement points, in which FIG. 6A is a plan view of scanning loci passing through a plurality of measurement points (in this example, 13 points) indicated by black circles, and FIG. 6B is a perspective view showing an association of the scanning loci shown in FIG. 6A and a needle-shaped recess 2A.

Since a planar shape of the conical needle-shaped recess 2A formed in the mold 2 is a circle, it is preferable that the plurality of measurement points on the surface of the drug solution 4 are disposed to be equivalent on polar coordinates in which a central position (the top of a cone) of the needle-shaped recess 2A is the origin.

In the first embodiment of the plurality of measurement points shown in FIG. 6A, the measurement points are disposed at equal intervals on two scanning line that are perpendicular to each other at a central position of the needle-shaped recess 2A (FIG. 2B). Thus, the measurement points are disposed at equidistant positions on a plurality of concentric circles in which the central position of the needle-shaped recess 2A is the center thereof.

That is, the plurality of measurement points of the first embodiment shown in FIG. 6A are symmetrical with respect to the central position of the needle-shaped recess 2A, are disposed at equal intervals on the concentric circles around the central position, and are disposed to match features of the surface shape of the drug solution 4.

Figure 7:
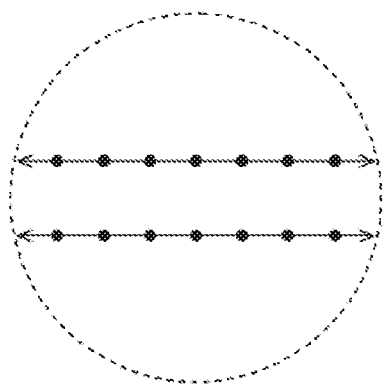
FIG. 7 is a plan view of scanning lines in a case where a plurality of measurement points are disposed on parallel two scanning lines.

FIG. 7 is a plan view of scanning lines in a case where a plurality of measurement points (14 points) are disposed on two parallel scanning lines, which is a diagram showing a modified example of the first embodiment of the plurality of measurement points.

The embodiment in FIG. 7 shows measurement points which are disposed at equal intervals on two scanning lines, similar to the first embodiment of the plurality of measurement points shown in FIG. 6A, but there is a bias in the disposition of the measurement points compared with the first embodiment, which is not preferable.

FIGS. 8A and 8B are diagrams showing an embodiment in a case where a new point (evaluation point) is calculated by interpolation of a plurality of measurement points, and particularly, show a case where the plurality of measurement points which are measured in the first embodiment shown in FIG. 6A are interpolated.

That is, z coordinates of intermediate positions on the same concentric circles are calculated through spline interpolation on the basis of a plurality of measurement points which are measured on the same concentric circles, which are the plurality of measurement points of the first embodiment shown in FIG. 8A (the same measurement points as the measurement points shown in FIG. 6A), and the calculated points are used as evaluation points.

FIG. 8B shows measured 13 measurement points which are indicated by black circles, and 12 evaluation points which are indicated by white circles which are generated through interpolation. The 12 evaluation points which are calculated in this way may be added to the 13 measurement points, and in this case, it is possible to acquire 25 (=13 points+12 points) three-dimensional positions on the surface of the drug solution 4.

Figure 9:
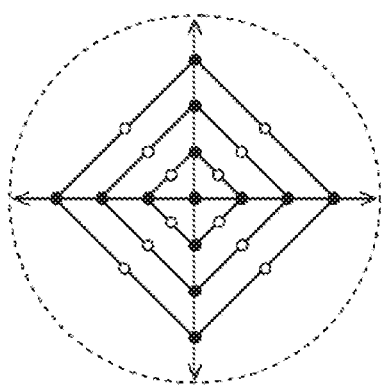
FIG. 9 is a diagram showing a case where contiguous measurement points among 13 measurement points which are measured are linearly interpolated to calculate 12 evaluation points.

FIG. 9 shows a case where adjacent measurement points among 13 measurement points which are measured are linearly interpolated to calculate 12 evaluation points. The 12 evaluation points which are indicated by white circles in FIG. 9 deviate from the features (shape continuously to the concentric circle shape) of the surface shape of the drug solution 4, and thus, are not preferable compared with the 12 evaluation points shown in FIG. 8B.

Second Embodiment of a Plurality of Measurement Points

FIGS. 10A and 10B are diagrams showing a second embodiment of a plurality of measurement points, in which FIG. 10A shows a case where 9 measurement points are disposed in a square lattice form and FIG. 10B shows 9 measurement points indicated by black circles, which are measured, and 8 evaluation points indicated by white circles, which are generated through interpolation.

As shown in FIG. 10A, the 9 measurement points which are disposed in the square lattice shape include a central position of the needle-shaped recess 2A, and two sets of four points which are respectively disposed on two concentric circles having different radii from the central position. Further, the two sets of four points which are respectively disposed on the two concentric circles are separated from each other at an angle difference of 45 degrees in a radial direction.

That is, the plurality of measurement points in the second embodiment shown in FIG. 10A are disposed at equidistant positions on the plurality of concentric circles around the central position of the needle-shaped recess 2A, which match the features of the surface shape of the drug solution 4.

Further, as shown in FIG. 10B, 8 evaluation points indicated by white circles, which are generated through interpolation, are points obtained by calculating z coordinates of intermediate positions on the same concentric circles through spline interpolation on the basis of a plurality of measurement points which are measured on the same concentric circles.

The 8 evaluation points calculated in this way may be added to the 9 measurement points which are measured, and in this case, it is possible to acquire three-dimensional positions of 17 points (=9 points+8 points) of the surface of the drug solution 4.

Third Embodiment of a Plurality of Measurement Points

Figure 11A:
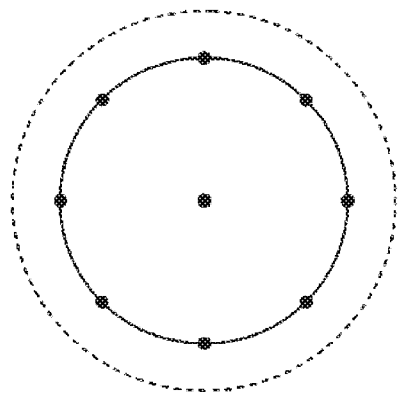
FIGS. 11A and 11B are diagrams showing a third embodiment of a plurality of measurement points.
Figure 11B:
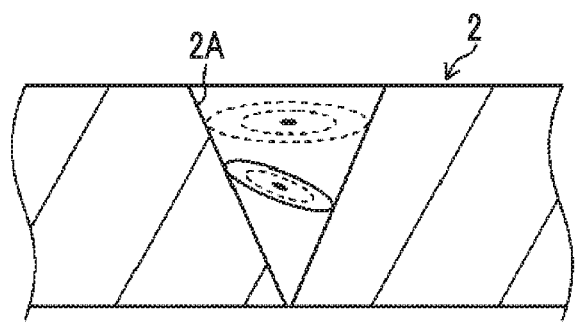

FIGS. 11A and 11B are diagrams showing a third embodiment of a plurality of measurement points, in which FIG. 11A is a plan view of a scanning locus passing through a plurality of measurement points (in this example, 9 points) indicated by black circles, and FIG. 11B is a perspective view showing an association of the scanning locus shown in FIG. 11A and the needle-shaped recess 2A.

The 9 measurement points shown in FIG. 11A include one point at a central position of the needle-shaped recess 2A, and 8 points which are disposed at equal intervals on a scanning line which represents circular scanning around the central position of the needle-shaped recess 2A.

That is, the plurality of measurement points in the third embodiment shown in FIG. 10A are disposed at equidistant positions on a circle around the central position of the needle-shaped recess 2A, which match the features of the surface shape of the drug solution 4.

Returning to FIG. 3, position information (x, y) of the plurality of measurement points shown in the above-described embodiments is stored in the storage unit 20. It is assumed that position information (x, y) of 13 measurement points in the first embodiment shown in FIG. 6A is stored in the storage unit 20.

The measurement unit 10 reads position information (x, y) of one measurement point among the position information (x, y) of the 13 measurement points stored in the storage unit 20, moves the table movement unit 116 on the basis of the read position information (x, y) of the measurement point, irradiates measurement light onto the measurement point indicated by the read position information (x, y), and detects a height-directional position (the position z in the Z-axial direction) of the measurement point irradiated with the measurement light, By repeating such a measurement operation by the number of the 13 measurement points stored in the storage unit 20, it is possible to acquire three-dimensional position information (x, y, z) of 13 measurement points on the surface of the drug solution 4 specified by the position information (x, y) of the 13 measurement points and information about the measured height position z.

Each piece of the position information (x, y, z) of 13 measurement points measured by the measurement unit 10 is output to the surface shape calculation unit 30 and the evaluation point calculation unit 40.

The evaluation point calculation unit 40 is a unit that interpolates measurement results of a plurality of measurement points in at least one direction among a deflection angle direction and a radial direction in a polar coordinate space in which the position of the center of the needle-shaped recess 2A is the origin of polar coordinates and calculates new evaluation points. In this example, the evaluation point calculation unit 40 calculates position information (x, y, z) of 12 evaluation points indicated by white circles on the basis of the position information (x, y, z) of 13 measurement points indicated by black circles as shown in FIGS. 8A and 8B. The position information (x, y, z) of the 12 evaluation points is calculated by performing non-linear interpolation (spline interpolation) with respect to position information of a plurality of measurement points on the same concentric circles.

The position information (x, y, z) of the 12 evaluation points calculated by the evaluation point calculation unit 40 is output to the surface shape calculation unit 30.

The surface shape calculation unit 30 calculates a three-dimensional shape of the surface of the drug solution 4 on the basis of the position information (x, y, z) of the 13 measurement points input from the measurement unit 10 and the position information (x, y, z) of the 12 evaluation points input from the evaluation point calculation unit 40. Details of a method for calculating the three-dimensional shape of the surface of the drug solution 4 in the surface shape calculation unit 30 will be described later.

Information indicating the three-dimensional shape of the surface of the drug solution 4 calculated by the evaluation point calculation unit 40 is output to the volume calculation unit 50. Information indicating the three-dimensional shape of the needle-shaped recess 2A of the mold 2 is input in advance to the volume calculation unit 50. The volume calculation unit 50 calculates, on the basis of the information indicating the three-dimensional shape of the surface of the drug solution 4 and the information indicating the three-dimensional shape of the needle-shaped recess 2A, a space (that is, the volume of the drug solution 4) formed by the three-dimensional shape of the surface of the drug solution 4 and the three-dimensional shape of the needle-shaped recess 2A.

Information indicating the volume of the drug solution 4 calculated by the volume calculation unit 50 is provided to the output unit 60.

The output unit 60 is a calculator that calculate the weight of the first polymer layer (the weight of the drug included in the first polymer layer) from the volume of the drug solution 4, a recording device that records the volume of the drug solution 4 in a hard disk device or the like, a display device that displays the volume of the drug solution 4, a printer that displays the volume of the drug solution 4, or an interface that outputs information indicating the volume of the drug solution 4 to these devices.

Since the volume of the drug solution 4 can be calculated as described above, it is possible to calculate the weight of the first polymer layer including the drug, the weight of the drug included in the first polymer layer, or the like with high accuracy from the volume of the drug solution 4. Further, since the needle-shaped recesses 2A corresponding to about 100 micro-needles are formed in the mold 2, the measurement system 1 measures the volume of the drug solution 4 that fills all the needle-shaped recesses 2A formed in the mold 2. Thus, it is possible to measure the weight of the drug corresponding to one MNA sheet with high accuracy in a non-contact manner before the MNA sheet is manufactured.

It is preferable that a measurement result measured by the measurement system 1 is fed back to an MNA sheet manufacturing process.

For example, in a case where the total volume of the drug solution 4 is smaller than a target value (or a lower limit value in a target range), a method for decreasing the speed of the squeegee 6 or increasing the amount of the drug solution 4 to be supplied onto the mold 2 may be considered, and in a case where the total volume of the drug solution 4 is larger than the target value (or an upper limit value in the target range), a method for increasing the speed of the squeegee 6 or decreasing the amount of the drug solution 4 to be supplied onto the mold 2 may be considered.

[Calculation Method of Three-Dimensional Shape of Surface of Drug Solution]

Next, a method for calculating the three-dimensional shape of the surface of the drug solution 4 in the surface shape calculation unit 30 will be described.

First Embodiment

The position information (x, y, z) of the 13 measurement points from the measurement unit 10 and the position information (x, y, z) of the 12 evaluation points from the evaluation point calculation unit 40 are provided to the surface shape calculation unit 30. The surface shape calculation unit 30 calculates the three-dimensional shape of the surface of the drug solution 4 on the basis of three-dimensional positions of these 25 points (=13 points+12 points) on the surface of the drug solution 4.

The surface shape calculation unit 30 performs non-linear interpolation on the basis of the three-dimensional positions of the 25 points on the surface of the drug solution 4, and calculates three-dimensional positions of multiple positions (for example, positions of 10000 points of 100×100) indicating the surface shape of the drug solution 4.

As the non-linear interpolation, any interpolation among polynomial interpolation of a two or higher order, spline interpolation (including B-spline curve interpolation), and Lagrange interpolation may be used.

Further, when the non-linear interpolation is performed on the basis of the three-dimensional positions of 25 points on the surface of the drug solution 4, it is preferable that the surface shape calculation unit 30 performs fitting so as to satisfy feature information of the three-dimensional shape of the surface of the drug solution to calculate the three-dimensional shape of the surface of the drug solution 4. The feature information of the three-dimensional shape of the surface of the drug solution may include unevenness conditions of the surface of the drug solution, for example.

Second Embodiment

Figure 12:
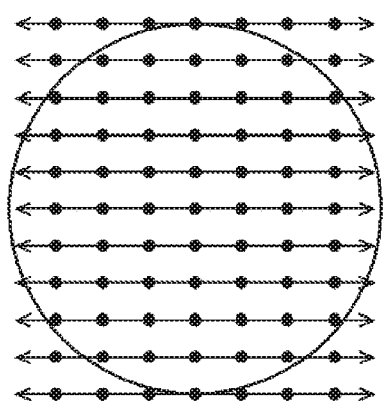
FIG. 12 is a plan view showing scanning lines for scanning measurement of multiple measurement points so as to measure a surface shape of a drug solution with high accuracy.

As shown in FIG. 12, the measurement unit 10 (the confocal microscope 100 shown in FIGS. 4 and 5) measures the heights (positions z in the z-axial direction) of 100×100 measurement points in a region of the surface (in a circle indicating an upper surface of the needle-shaped recess 2A) of the drug solution 4 in advance, to thereby measure the surface shape of the drug solution 4 with high accuracy. In a case where the multiple measurement points are measured, the measurement time becomes long, but since the highly accurate measurement is performed only with respect to a plurality of models (models of the drug solution 4), the measurement time does not cause any problem.

The surface shape calculation unit 30 sets the surface shapes of a plurality of models measured in advance with high accuracy as described above as predict information, and causes three-dimensional positions of the 25 points on the surface of the drug solution 4 to be fitted to a model including a feature amount of the three-dimensional shape of the surface of the drug solution, on the basis of the predict information and the three-dimensional positions of the 25 points on the surface of the drug solution 4, to thereby calculate the three-dimensional shape of the surface of the drug solution 4.

The surface shape calculation unit 30 sets the surface shapes of the plurality of models measured in advance with high accuracy, as the predict information, and calculates the three-dimensional shape of the surface of the drug solution 4 from the three-dimensional position of a small number of measurement points using main component analysis (singular value decomposition), recursive filtering, independent component analysis, fractal analysis, or the like.

[Measurement Method]

Next, an embodiment of a measurement method according to the invention will be described.

Figure 13:
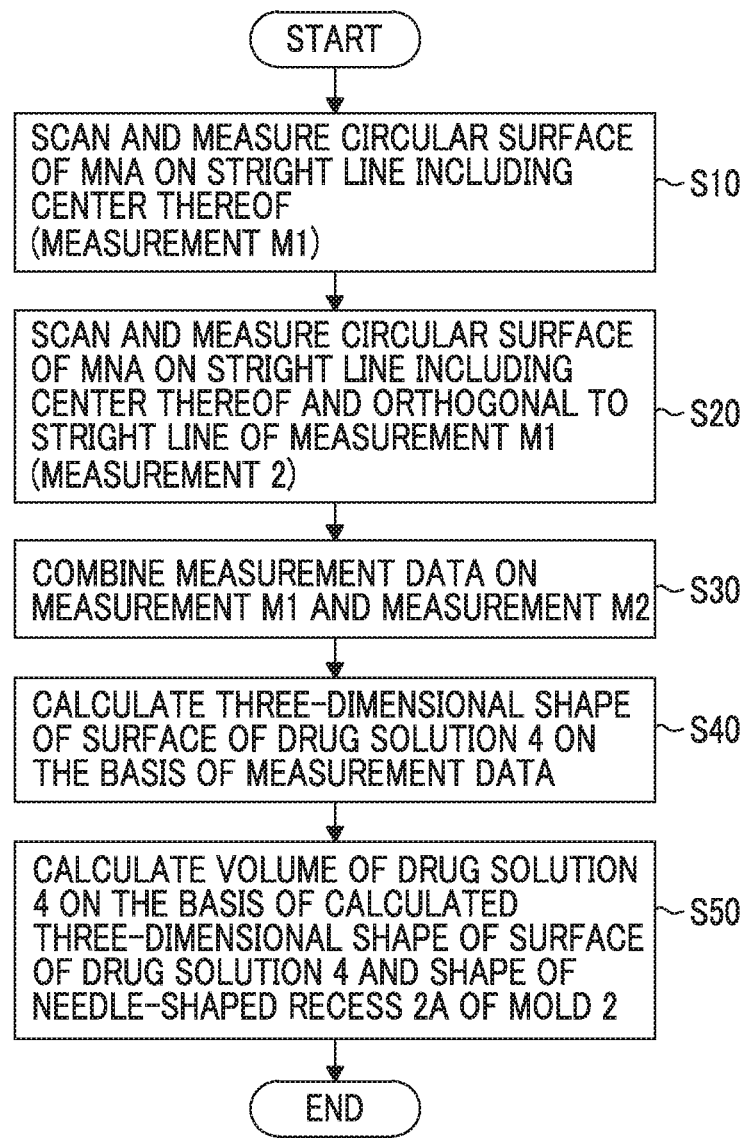
FIG. 13 is a flowchart showing an embodiment of a measurement method according to the invention.

FIG. 13 is a flowchart showing an embodiment of a measurement method according to the invention. In this embodiment, a case where the plurality of measurement points (13 points) shown in FIG. 6A are used will be described.

In FIG. 13, a circular surface of the MNA (needle-shaped recesses 2A) of the surface of the mold 2 is scanned and measured on a straight line including the center thereof by the measurement unit 10 (measurement M1) (step S10). That is, in the measurement M1, positions on the surface of the drug solution 4 that fills the needle-shaped recesses 2A, that is, positions z, in the height direction, of 7 measurement points on a straight line including the center of the needle-shaped recesses 2A (black circles in FIG. 6A in the lateral direction) are measured.

Similarly, the circular surface of the MNA of the surface of the mold 2 is scanned and measured on a straight line including the center thereof and orthogonal to the straight line of the measurement M1 by the measurement unit 10 (measurement M2) (step S20). That is, in the measurement M2, positions on the surface of the drug solution 4 that fills the needle-shaped recesses 2A, that is, positions z, in the height direction, of 6 measurement points on a straight line including the center of the needle-shaped recesses 2A (black circles in the vertical direction except the center of FIG. 6A) are measured.

Subsequently, measurement data on the measurement M1 and measurement data on the measurement M2 are combined to acquire a position (x, y, z) on the surface of the drug solution 4 of 13 points (=7+6) (step S30).

Then, a three-dimensional shape of the surface of the drug solution 4 is calculated on the basis of measurement data on the 13 measurement points on the surface of the drug solution 4 acquired in this way (step S40). The three-dimensional shape of the surface of the drug solution 4 is calculated by performing non-linear interpolation with respect to the measurement data on the 13 points, or is calculated by setting surface shapes of a plurality of models as predict information and using a method such as main component analysis on the basis of the predict information and the measurement data on the 13 points of the surface of the drug solution 4.

Thereafter, the volume of the drug solution 4 is calculated on the basis of the three-dimensional shape of the surface of the drug solution 4 calculated in this way and the three-dimensional shapes (known shapes) of the needle-shaped recesses 2A of the mold 2 (step S50).

<Method for Calculating Surface Shape of Drug Solution Using Main Component Analysis Method>

Next, a method for calculating a surface shape of a drug solution using a main component analysis method will be described with reference to FIGS. 14 and 15.

Figure 14:
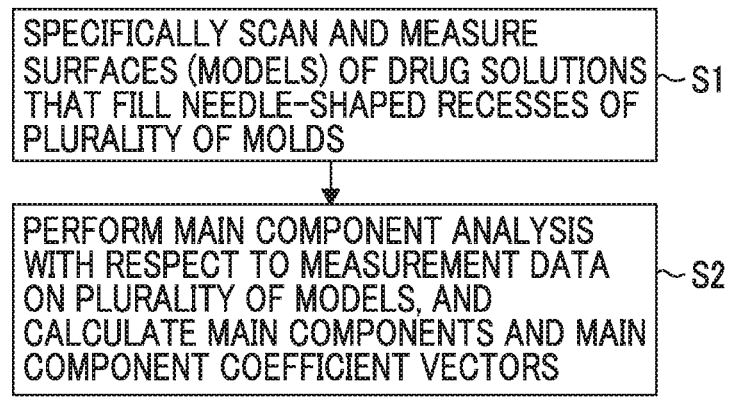
FIG. 14 is a diagram showing a pre-treatment in a case where a surface shape of a drug solution is calculated using a main component analysis method.

As shown in FIG. 14, first, a surface (model) of a drug solution that fills needle-shaped recesses of a plurality of molds is scanned and measured in detail (step S1). The detailed measurement is performed by measuring positions of 10000 (=100×100) measurement points as described using FIG. 12.

Subsequently, the main component analysis is performed with respect to main components of measurement data on the plurality of molds to calculate the main components and main component coefficient vectors (step S2).

M main components $\{z_m\}$ are represented by the following expression.

$$z_m = \sum_{p=1}^{P} w_{pm} x_p \quad (m = 1, 2, \ldots, M) \quad \text{[Expression 1]}$$

The main component $\{z_m\}$ is given measurement data (in this example, measurement data of a plurality of models) of P variables $\{x_p\}$ (p=1, 2, ..., P) (in this example, P=10000 (the number of measurement points)) as a primary coupling of $\{x_p\}$ while reducing loss of information to a minimum. In Expression 1, $z_m$ is an m-th main component, and $w_{pm}$ is a coupling coefficient of the m-th main component. Here, the m-th main component m is a value capable of sufficiently securing information of P variables, and is an extremely small value compared with P in this example.

When a deviation of an n-th sample (measurement data of a model) in P measurement points is represented as $x_n$ ($x_n = x_{n1}, x_{n2}, \ldots, x_{nP}$), a value $t_{n1}$ (a first main component score) of a first main component $z_1$ with respect to $x_n$ may be expressed by the following expression.

$$t_{n1} = \sum_{p=1}^{P} w_p x_{np} \quad \text{[Expression 2]}$$

In a similar way, a second main component score $t_{n2}$ to an m-th main component score $t_{nm}$ may be calculated.

Coupling coefficients of the first main component to the m-th main component (hereinafter, referred to as "main component coefficient vectors") and the first main component score to the m-th main component score (hereinafter, referred to as "main components of models" are calculated on the basis of the measurement data on the plurality of models which are measured in advance as described above.

Figure 15:
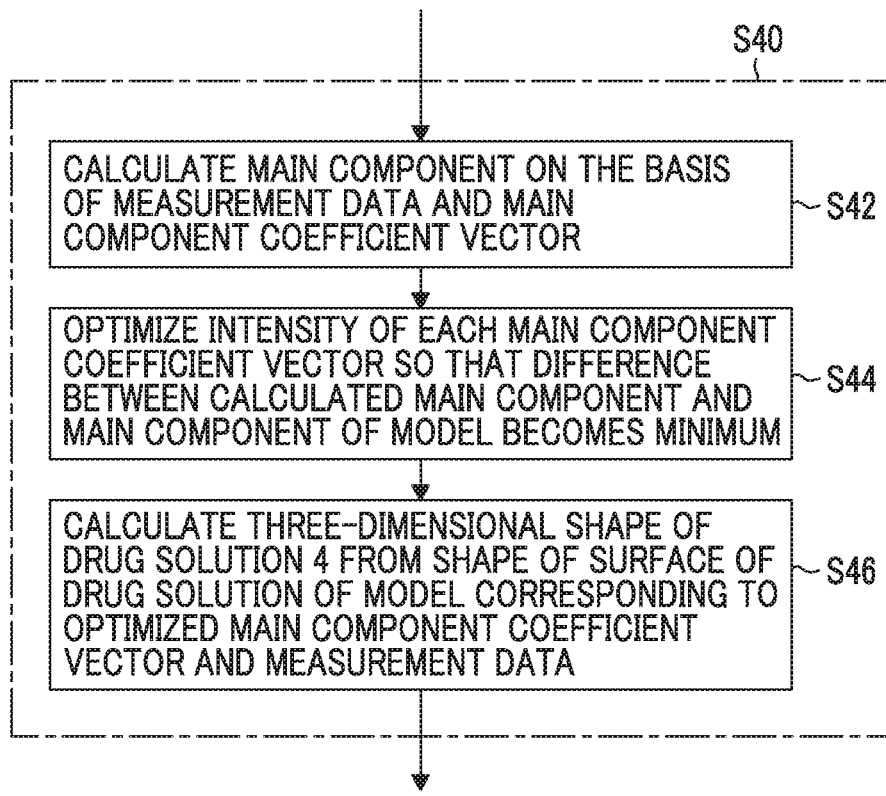
FIG. 15 is a flowchart showing specific processes of step S40 shown in FIG. 13, and particularly, is a flowchart showing a method for calculating the surface shape of the drug solution using the main component analysis method.

FIG. 15 is a flowchart showing a specific process of step S40 shown in FIG. 13, and particularly, is a flowchart showing a case where the surface shape of the drug solution is calculated using the main component analysis method.

In FIG. 15, on the basis of measurement data on 15 points on the surface of the drug solution 4 and the main component coefficient vectors that are calculated in advance on the basis of models, main components relating to the measurement data are calculated (step S42).

The intensity of each main component coefficient vector is optimized so that a difference between the main component calculated on the basis of the measurement data and the main component of the model becomes a minimum (step S44). The main component coefficient vector of the model when the difference between the main component of each model calculated for a plurality of models and the main component calculated on the basis of the measurement data becomes a minimum may be set as an optimized main component coefficient vector of the main component of the model.

Further, a three-dimensional shape of the drug solution 4 is calculated from the shape of the surface of the drug solution in the model corresponding to the optimized main component coefficient vector (specifically, the scanned and measured shape) and the measurement data (step S46).

Others

In this embodiment, the confocal microscope 100 is used as the measurement device 10, but the invention is not limited thereto, and for example, a triangulation type displacement meter may be applied.

Figure 16:
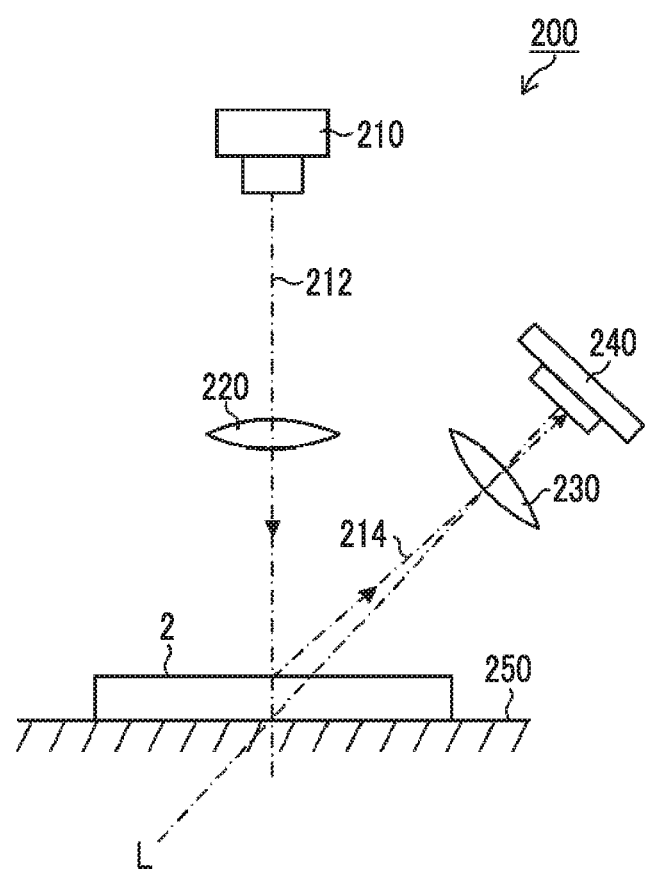
FIG. 16 is a diagram showing a measurement principle based on a triangulation method of a triangulation type displacement meter.

FIG. 16 is a diagram showing a measurement principle based on a triangulation method of a triangulation type displacement meter 200.

As shown in FIG. 16, a measurement head unit of the triangulation type displacement meter 200 includes a semiconductor laser 210, a projection lens 220, a light receiving lens 230, and a light position sensor 240. The semiconductor laser 210 emits laser light 212 in a direction (vertical direction) orthogonal to a horizontal table 250. The laser light 212 emitted from the semiconductor laser 210 is incident to a measurement point on a surface of a drug solution that fills a mold 2, which is a measurement target surface, as spot light through the projection lens 220, and part of the spot light is reflected from the surface of the drug solution.

Reflected light 214 that is reflected from the measurement point on the surface of the drug solution is image-formed on a light receiving surface of the light position sensor 240 through the light receiving lens 230. A light receiving unit that includes the light receiving lens 230 and the light position sensor 240 in this example is disposed so that an optical axis L of the light receiving unit intersects the laser light 212 on the table 250.

The triangulation type displacement meter 200 reads a light receiving position of the reflected light 214 in the light position sensor 240, and measures the height of the surface of the drug solution with reference to a front surface (of the table 250 a bottom surface of the mold 2) on the basis of the read light receiving position.

Further, the number of a plurality of measurement points on the surface of the drug solution and an arrangement thereof are not limited to this embodiment, and various modifications may be made in a range without departing from the concept of the invention.

In addition, the shape of the MNA (the shape of a needle-shaped recess formed in a mold) is not limited to a conical shape, and for example, a pyramid shape such as a quadrangular pyramid shape may be used. Furthermore, it is preferable to perform surface treatment for enhancing a hydrophilic property with respect to the front surface of the mold. Accordingly, a contact angle of a drug solution that fills a needle-shaped recess decreases, and thus, it is possible to bring the surface of the drug solution close to horizontal.

In order to increase the reflectivity of the measurement light on a surface of a drug solution, it is preferable to add a coloring matter (for example, Evans' blue) which is harmless to the human body to the drug solution.

Further, in a case where a surface shape of a drug solution is measured, it is preferable to measure positions of a plurality of measurement points under an environment that the humidity is 100% or in a state where an upper side of a mold that is filled with the drug solution is covered with a transparent cover so that the drug solution is not naturally dried.

Furthermore, the above-described respective functional configurations of the measurement system may be appropriately realized by arbitrary hardware, software, or a combination thereof. For example, the invention may also be applied to a measurement program that causes a computer to execute measurement methods (measurement processing procedures) in the above-described respective devices and processing units (the measurement unit 10, the storage unit 20, the surface shape calculation unit 30, and the volume calculation unit 50), a computer-readable recording medium (non-transitory tangible medium) on which the measurement program is recorded, or a computer in which the measurement program can be installed.

EXPLANATION OF REFERENCES

1: measurement system
2: mold
2A: needle-shaped recess
2B: air vent port
4: drug solution
4A: drug
6: squeegee
10: measurement unit
20: storage unit
30: surface shape calculation unit
40: evaluation point calculation unit
50: volume calculation unit
60: output unit
100: confocal microscope

What is claimed is:

1. A measurement system that measures an amount of a drug solution that fills each needle-shaped recess of a sheet-shaped mold in which a plurality of the needle-shaped recesses are formed, each of the needle-shaped recesses being an inverted type of a micro-needle, or an amount of a drug after the filled drug solution is dried, the system comprising:

a measurement unit that measures respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried;

a surface shape calculation unit that calculates a three-dimensional shape of the surface of the drug solution or the surface of the drug on the basis of the heights of the plurality of measurement points measured by the measurement unit; and a volume calculation unit that calculates the volume of the drug solution that fills the needle-shaped recess or the drug after the filled drug solution is dried on the basis of the three-dimensional shape of the surface of the drug solution or the surface of the drug, calculated by the surface shape calculation unit, and the shape of the needle-shaped recess of the mold, wherein the surface shape calculation unit calculates the three-dimensional shape of the surface of the drug solution or the surface of the drug, using three-dimensional positions of the plurality of measurement points specified by positions of the plurality of measurement points on the plane and the heights of the plurality of measurement points measured by the measurement unit, and using predict information relating to the three-dimensional shape of the surface of the drug solution or the surface of the drug.

2. The measurement system according to claim 1,
wherein the plurality of preset measurement points include a plurality of measurement points disposed at equal intervals on a scanning line.

3. The measurement system according to claim 1,
wherein the plurality of preset measurement points are symmetrical with respect to a central position of the needle-shaped recess and correspond to a plurality of positions disposed at equal intervals on concentric circles in which the central position is the center.

4. The measurement system according to claim 3,
wherein the plurality of preset measurement points correspond to a plurality of positions disposed on two lines that are orthogonal to each other at the central position of the needle-shaped recess.

5. The measurement system according to claim 3, further comprising
an evaluation point calculation unit that interpolates measurement results of the plurality of measurement points in at least one direction among a deflection angle direction and a radial direction in a polar coordinate space in which the central position of the needle-shaped recess is the origin of polar coordinates to calculate new evaluation points,
wherein the calculated new evaluation points are added to the plurality of measurement points.

6. A measurement system that measures an amount of a drug solution that fills each needle-shaped recess of a sheet-shaped mold in which a plurality of the needle-shaped recesses are formed, each of the needle-shaped recesses being an inverted type of a micro-needle, or an amount of a drug after the filled drug solution is dried, the system comprising:
a measurement unit that measures respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried;
a surface shape calculation unit that calculates a three-dimensional shape of the surface of the drug solution or the surface of the drug on the basis of the heights of the plurality of measurement points measured by the measurement unit; and
a volume calculation unit that calculates the volume of the drug solution that fills the needle-shaped recess or the drug after the filled drug solution is dried on the basis of the three-dimensional shape of the surface of the drug solution or the surface of the drug, calculated by the surface shape calculation unit, and the shape of the needle-shaped recess of the mold,
wherein the surface shape calculation unit calculates the three-dimensional shape of the surface of the drug solution or the surface of the drug by causing three-dimensional positions of the plurality of measurement points specified by positions of the plurality of measurement points on the plane and the heights of the plurality of measurement points measured by the measurement unit to be fitted to a model including a feature amount of the three-dimensional shape of the surface of the drug solution or the surface of the drug, which is measured in advance, to calculate the three-dimensional shape of the surface of the drug solution or the surface of the drug.

7. The measurement system according to claim 6,
wherein the model including the feature amount of the three-dimensional shape is formed by main component coefficient vectors extracted from a plurality of three-dimensional shapes obtained in advance by measurement of a plurality of samples on the surface of the drug solution or the surface of the drug.

8. The measurement system according to claim 1,
wherein the measurement unit is a confocal microscope that measures the heights on the surface of the drug solution that fills the needle-shaped recess or on the surface of the dried drug after filling using a confocal optical system, or a triangulation type displacement meter that measures the heights on the surface of the drug solution that fills the needle-shaped recess or on the surface of the dried drug after filling using a triangulation type displacement method.

9. A measurement method for measuring an amount of a drug solution that fills each needle-shaped recess of a sheet-shaped mold in which a plurality of the needle-shaped recesses are formed, each of the needle-shaped recesses being an inverted type of a micro-needle, or an amount of a drug after the filled drug solution is dried, the method comprising:
a step of measuring respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried;
a step of calculating a three-dimensional shape of the surface of the drug solution or the surface of the drug on the basis of the measured heights of the plurality of measurement points; and
a step of calculating the volume of the drug solution that fills the needle-shaped recess or the drug after the filled drug solution is dried on the basis of the calculated three-dimensional shape of the surface of the drug solution or the surface of the drug and the shape of the needle-shaped recess of the mold,
wherein the step of calculating the three-dimensional shape of the surface of the drug solution or the surface of the drug, comprises using—three-dimensional positions of the plurality of measurement points specified by positions of the plurality of measurement points on the plane and the heights of the plurality of measurement points measured in the measuring step, and using predict information relating to the three-dimensional shape of the surface of the drug solution or the surface of the drug.

10. The measurement method according to claim 9,
wherein the plurality of preset measurement points include a plurality of measurement points disposed at equal intervals on a scanning line.

11. The measurement method according to claim 9,
wherein the plurality of preset measurement points are symmetrical with respect to a central position of the needle-shaped recess and correspond to a plurality of positions disposed at equal intervals on concentric circles in which the central position is the center.

12. A computer-readable non-transitory tangible recording medium which records a program that causes a computer to execute a measurement method for measuring an amount of a drug solution that fills each needle-shaped recess of a sheet-shaped mold in which a plurality of the needle-shaped recesses are formed, each of the needle-shaped recesses being an inverted type of a micro-needle, or an amount of a drug after the filled drug solution is dried, the program causing the computer to execute:
- a step of measuring respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried;
- a step of calculating a three-dimensional shape of the surface of the drug solution or the surface of the drug on the basis of the measured heights of the plurality of measurement points; and
- a step of calculating the volume of the drug solution that fills the needle-shaped recess or the drug after the filled drug solution is dried on the basis of the calculated three-dimensional shape of the surface of the drug solution or the surface of the drug and the shape of the needle-shaped recess of the mold,
- wherein the step of calculating the three-dimensional shape of the surface of the drug solution or the surface of the drug, comprises using—three-dimensional positions of the plurality of measurement points specified by positions of the plurality of measurement points on the plane and the heights of the plurality of measurement points measured in the measuring step, and using predict information relating to the three-dimensional shape of the surface of the drug solution or the surface of the drug.

13. The computer-readable non-transitory tangible recording medium according to claim 12,
wherein the plurality of preset measurement points include a plurality of measurement points disposed at equal intervals on a scanning line.

14. The computer-readable non-transitory tangible recording medium according to claim 12,
wherein the plurality of preset measurement points are symmetrical with respect to a central position of the needle-shaped recess and correspond to a plurality of positions disposed at equal intervals on concentric circles in which the central position is the center.

15. The measurement system according to claim 6,
wherein the plurality of preset measurement points include a plurality of measurement points disposed at equal intervals on a scanning line.

16. The measurement system according to claim 6,
wherein the plurality of preset measurement points are symmetrical with respect to a
central position of the needle-shaped recess and correspond to a plurality of positions disposed at
equal intervals on concentric circles in which the central position is the center.

17. The measurement system according to claim 6,
wherein the plurality of preset measurement points are symmetrical with respect to a central position of the needle-shaped recess and correspond to a plurality of positions disposed at equal intervals on concentric circles in which the central position is the center, and
wherein the plurality of preset measurement points correspond to a plurality of positions disposed on two lines that are orthogonal to each other at the central position of the needle-shaped recess.

18. The measurement system according to claim 6,
wherein the plurality of preset measurement points are symmetrical with respect to a central position of the needle-shaped recess and correspond to a plurality of positions disposed at equal intervals on concentric circles in which the central position is the center, and further comprising:
an evaluation point calculation unit that interpolates measurement results of the plurality of measurement points in at least one direction among a deflection angle direction and a radial direction in a polar coordinate space in which the central position of the needle-shaped recess is the origin of polar coordinates to calculate new evaluation points,
wherein the calculated new evaluation points are added to the plurality of measurement points.

19. The measurement system according to claim 6,
wherein the measurement unit is a confocal microscope that measures the heights on the surface of the drug solution that fills the needle-shaped recess or on the surface of the dried drug after filling using a confocal optical system, or a triangulation type displacement meter that measures the heights on the surface of the drug solution that fills the needle-shaped recess or on the surface of the dried drug after filling using a triangulation type displacement method.

20. A measurement method for measuring an amount of a drug solution that fills each needle-shaped recess of a sheet-shaped mold in which a plurality of the needle-shaped recesses are formed, each of the needle-shaped recesses being an inverted type of a micro-needle, or an amount of a drug after the filled drug solution is dried, the method comprising:
- a step of measuring respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried;
- a step of calculating a three-dimensional shape of the surface of the drug solution or the surface of the drug on the basis of the measured heights of the plurality of measurement points; and
- a step of calculating the volume of the drug solution that fills the needle-shaped recess or the drug after the filled drug solution is dried on the basis of the calculated three-dimensional shape of the surface of the drug solution or the surface of the drug and the shape of the needle-shaped recess of the mold,
- wherein the step of calculating the three-dimensional shape of the surface of the drug solution or the surface of the drug comprises causing three-dimensional positions of the plurality of measurement points specified by positions of the plurality of measurement points on the plane and the heights of the plurality of measurement points measured in the measuring step to be fitted to a model including a feature amount of the three-dimensional shape of the surface of the drug solution or the surface of the drug, which is measured in advance, to calculate the three-dimensional shape of the surface of the drug solution or the surface of the drug.

21. The measurement method according to claim 20,
wherein the plurality of preset measurement points include a plurality of measurement points disposed at equal intervals on a scanning line.

22. The measurement method according to claim 20,
wherein the plurality of preset measurement points are symmetrical with respect to a central position of the needle-shaped recess and correspond to a plurality of positions disposed at equal intervals on concentric circles in which the central position is the center.

23. A computer-readable non-transitory tangible recording medium which records a program that causes a computer to execute a measurement method for measuring an amount of a drug solution that fills each needle-shaped recess of a sheet-shaped mold in which a plurality of the needle-shaped recesses are formed, each of the needle-shaped recesses being an inverted type of a micro-needle, or an amount of a drug after the filled drug solution is dried, the program causing the computer to execute:

- a step of measuring respective heights of a plurality of measurement points preset on a plane parallel to the mold, in a direction orthogonal to the plane, which are heights on a surface of the drug solution that fills the needle-shaped recess or heights on a surface of the drug after the filled drug solution is dried;
- a step of calculating a three-dimensional shape of the surface of the drug solution or the surface of the drug on the basis of the measured heights of the plurality of measurement points; and
- a step of calculating the volume of the drug solution that fills the needle-shaped recess or the drug after the filled drug solution is dried on the basis of the calculated three-dimensional shape of the surface of the drug solution or the surface of the drug and the shape of the needle-shaped recess of the mold, wherein the step of calculating the three-dimensional shape of the surface of the drug solution or the surface of the drug comprises causing three-dimensional positions of the plurality of measurement points specified by positions of the plurality of measurement points on the plane and the heights of the plurality of measurement points measured in the measuring step to be fitted to a model including a feature amount of the three-dimensional shape of the surface of the drug solution or the surface of the drug, which is measured in advance, to calculate the three-dimensional shape of the surface of the drug solution or the surface of the drug.

24. The computer-readable non-transitory tangible recording medium according to claim 23, wherein the plurality of preset measurement points include a plurality of measurement points disposed at equal intervals on a scanning line.

25. The computer-readable non-transitory tangible recording medium according to claim 23, wherein the plurality of preset measurement points are symmetrical with respect to a central position of the needle-shaped recess and correspond to a plurality of positions disposed at equal intervals on concentric circles in which the central position is the center.

* * * * *